(12) United States Patent
Levisman (10) Patent No.: US 6,350,126 B1
(45) Date of Patent: Feb. 26, 2002

(54) BONE IMPLANT

(76) Inventor: Ricardo Levisman, Aguero 1292-1° piso, 1425 Cuidad de Buenos Aires (AR)

(*) Notice: Subject to any disclaimer, the term of this patent is extended or adjusted under 35 U.S.C. 154(b) by 0 days.

(21) Appl. No.: 09/654,155

(22) Filed: Sep. 1, 2000

(51) Int. Cl.[7] .................................................. A61C 8/00
(52) U.S. Cl. .......................... 433/173; 433/174; 433/1
(58) Field of Search ................................ 433/172, 173, 433/174

(56) References Cited

U.S. PATENT DOCUMENTS

| | | | | |
|---|---|---|---|---|
| 3,708,883 A | * | 1/1973 | Flander | 433/174 |
| 5,004,420 A | * | 4/1991 | Soderberg | 433/172 |
| 5,004,421 A | | 4/1991 | Lazarof | 433/173 |
| 5,087,199 A | | 2/1992 | Lazarof | 433/173 |
| 5,125,840 A | * | 6/1992 | Durr et al. | 433/173 |
| 5,417,569 A | * | 5/1995 | Perisse | 433/174 |
| 5,489,210 A | | 2/1996 | Hanosh | 433/173 |
| 5,611,688 A | | 3/1997 | Hanosh | 433/174 |
| 5,681,167 A | * | 10/1997 | Lazarof | 433/174 |
| 5,890,902 A | * | 4/1999 | Sapian | 433/173 |
| 5,931,674 A | * | 8/1999 | Hanosh et al. | 433/173 |

FOREIGN PATENT DOCUMENTS

| WO | WO-93011717 A | * | 6/1993 | | 433/173 |
|---|---|---|---|---|---|

OTHER PUBLICATIONS

Cranin, Norman, *Atlas of Oral Implantology*, 2nd Ed., St. Louis, Mosby, 1999, pp. 326 and 343.

* cited by examiner

*Primary Examiner*—Cary E. O'Connor
(74) *Attorney, Agent, or Firm*—Greer, Burns & Crain, Ltd.

(57) ABSTRACT

A bone implant for fixing a fixing stud of a dental prosthesis into a bone, the implant being a non-expandable or an expandable implant comprising a tubular body and an intermediate mounting member removably mounted into the body, the intermediate member receiving the fixing stud and being capable of being removed from the body even after a long time of the implantation of the implant, thus permitting the removal of the stud from the implant in the event the stud is broken within the implant.

20 Claims, 5 Drawing Sheets

BONE IMPLANT

BACKGROUND OF THE INVENTION

1. Field of the Invention

The present invention relates to a bone implant, preferably a bone implant for implanting prosthetic pieces in a bone, such as dental prosthesis in a jaw, the implant comprising a fixing piece or body to be affixed in a bone and a mounting intermediate member for receiving the prosthesis piece, the mounting member being capable of being removed without traumatic effects for the patient in the event that the prosthesis or a fixing stud thereof is broken. The intermediate member can be removed even after a long time with the fixing body already integrated into the bone. Of course, the concepts of the invention are easily applied to any implant piece that must be implanted in a human being or animal bone. In addition, the invention is not only applied to expandable implants, of the type that can be initially expanded to get a retention into the bone, but also to non expandable implants.

2. Description of the Prior Art

It is well known in medical art to provide bone implants that are useful for affixing a prosthetic piece in a bone, in replacement of any lacking natural piece or member or for joining parts of one or more bones. More, particularly, these implants are well known in odontology wherein dental implants are used for replacing a dental piece that has been lost or extracted either in a human or animal patient. One of the problems or traumatic drawbacks of implanting a dental prosthesis in a patient is that a long time is necessary to assure to the patient that the implant is entirely or totally integrated to the jaw of the patient. Generally, after the extraction or loss of the dental piece, a fixing body of the implant is inserted and implanted into the jaw and several months must be awaited to determine whether the fixing body has been integrated to the bone or bone fibers of the bore in the jaw, this determination being necessary to continue or not with the next step of affixing the prosthetic piece into the implant. If the body has not been integrated the same must be replaced and a new waiting period begins again. This provokes anxiety and affliction in the patient who must await for months before receiving a positive diagnostic from the odontologist or the implantologist and upon a negative diagnostic the patient knows that the fixing body must be removed and that several additional months must be awaited again. With the purpose of shortening this waiting periods some implants, either of the expandable or non expandable type have been developed. The expandable implants are based in the theory that greater pressure against the bone generates greater bone growth. These implants are installed within the bone orifice or bore resulting from the loosen or removed dental piece or within a bore made in the bone and the implant is radially expanded in order to get a positive initial pressure and retention. During the first weeks from the installation it is possible to verify whether micro-mobility exists and, if the micro-mobility is detected the implant is additionally expanded to improve the radial retention. The purpose of these additional expansions is to get the immobility of the fixing piece that is a fundamental condition to reach the integration of the piece into the bone. While these implants have been improved insofar as the micro mobility is concerned, the same have not taken into account an important aspect of the implants, that is the need of replacing a broken prosthesis after a long time from the integration of the implant into the bone.

Generally, prosthetic dental pieces are affixed to a fixation stud or abutment that is installed by threading or adhesive within the fixing or mounting body that is already integrated into the bone. During the use of the prosthetic piece, if the fixing stud is broken within the fixing body that is already integrated or implanted, the broken portion of the stud that remains within the implanted body must be removed before a new prosthetic piece is re-installed. Any professional skilled in the art knows that the removal of this broken stud in the small room of the patient's mouth is very difficult if not impossible. Said broken portion is not accessible and very frequently the portion cannot be extracted, therefore the implant body must be removed from its implantation by drilling the patient's jaw to release the fixing body from the jaw bone, which is very traumatic for the patient.

The initial fixation of the implant has been treated by several professionals and disclosed in many documents like the U.S. Pat. Nos. 5,004,421 and 5,087,199 to Lazarof, which disclose expandable implants having a fixing piece that is introduced and threaded into a patient's bone and has a hollow interior that is also threaded and a plurality of longitudinal cuts in the implant body. An expanding piece is arranged within the hollow interior, the piece being accessed from a top end of the fixing body by means of a tool that is introduced within the implant body to cause the expanding piece to rotate and move upwardly in order to expand the implant body to enhance the retention thereof into the bone. An upper portion of the fixation body has a threaded inner orifice for receiving a fixing stud or abutment of the dental prosthesis. While a better initial fixation is achieved no consideration is made to the event that the prosthesis stud is broken and the prosthesis is loosened.

U.S. Pat. No. 5,489,210 discloses a dental implant having a fixation body that is introduced within the body and has a plurality of longitudinal cuts at a lower end of the body, this lower end being expanded by an expanding piece that is introduced through an upper end into the implant body and exerts a pressure against the lower end of the body to outwardly radially expand the same against the bone. Again, the initial pressure of the implant against the bone is improved but a solution to the event of a broken stud is neither provided nor suggested. The stud of the prosthetic piece is mounted directly within the fixing body of the implant.

U.S. Pat. No. 5,611,688 discloses an expandable dental implant also comprising a hollow tubular outer body that is affixed by expansion into the bone, the expansion being obtained by an expanding screw that is inserted into the hollow body and the initial fixation of the implant is improved. This patent does not disclose any solution to the event that the prosthesis and its fixing stud are loosen or broken. In like manner, U.S. Pat. No. 5,931,674 discloses an expandable implant very similar to the '688 patent, but no means for permitting an easy removal of a broken fixing stud are provided, and the problem is not addressed.

It would be therefore convenient to have a new expandable or non expandable implant provided with means for enhancing the initial fixation of the implant within the bone and means for permitting the easy removal of the fixation stud of the prosthesis piece in the event the stud is broken with a portion of the stud remaining within an implant body already integrated to the bone.

SUMMARY OF THE INVENTION

It is therefore one object of the present invention to provide a bone implant for fixing a dental prosthesis into a bone, the prosthesis being fixed into an implant body by means of a fixing stud that is fixed into the body, in the event the stud is broken and the prosthesis is loosened the novel implant permitting the easy removal of a portion of the stud that remains within the body without the need of removing the body from the bone.

It is still another object of the present invention to provide a bone implant comprising a fixing tubular body for fixing in the bone, the tubular body including a distal end for being affixed within a bone bore and a proximal end for remaining accessible outside the bone and a prosthesis piece being received in the proximal end, the bone implant comprising a mounting intermediate member for mounting said prosthesis piece, the intermediate member being removably mounted within said tubular body, the intermediate member including a proximal end in communication with an inner surface for receiving a fixing stud of said prosthesis piece.

It is a further object of the present invention to provide a bone implant comprising a fixing tubular body for fixing in the bone, the tubular body including a distal end for being affixed within a bone bore and a proximal end for remaining accessible outside the bone and within the gum and for receiving a prosthesis piece, the distal end of the body including a plurality of longitudinal cuts that permit a lower portion of the body be radially outwardly expanded by an expanding member that is received within said body, said expanding member being fixed to a distal end of a stem having a proximal end within said tubular body and a threaded outer surface, the implant also comprising a rotatable mounting intermediate member that includes a threaded inner surface within which said stem is threadably received, the mounting intermediate member including an upper end receiving the prosthesis piece.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Now referring in detail to the drawings it may be seen from FIGS. 1–5 an expandable bone implant according to the invention that is identified by reference number 1 and comprises a fixation or fixing tubular body 2 having a distal end 3 and a proximal end 4 terminating in a coupling plate or coupling end 5 having a first cylindrical portion 6 and a second upper conical portion 7. The distal end is adapted to be introduced and remain within a bone 8 and more particularly within a bore or orifice 9 that can be made artificially in the bone or corresponds to the natural orifice resulting from the extraction or loosening of a natural tooth.

When the invention is applied to an expandable implant, distal end 3 includes a plurality of longitudinal cuts 10, preferably four cuts 10. These cuts define corresponding flexible portions or deformable tongues 11 that may be slightly tapered to facilitate the initial insertion of body 2 within orifice 9. Tongues 11 will be provided with the necessary elasticity for radially outwardly expanding as it will be further explained. The outer surface of body 2 may be smooth and plain or may be treated to enhance its adherence and obtain an improved body-bone integration. Thus, the surface may be treated and/or coated with hydroxyapatite, titanium plasma spray or acids. Depending on the bone hardness, for example, the body surface would be treated or coated, in less dense bone rough, the titanium plasma spray (TPS) and the hydroxyapatite (HA) coatings help as well by presenting maximal interfacial areas. The outer surface of body 2 may be provided with threads, notches, and indentations, and may be screw machined, acid etched, machined roughened, stepped, and combined with the above coatings. As an example, threads 12 are illustrated only at the right side in FIGS. 1, 4, 5, 6, 8–10, but, as it will be apparent to any person skilled in the art, threads 12, if provided, may extend all around the body or along a partial circumference around the body. Threads 12 may have any cross-section and configuration, preferably for obtaining a better grip between the fixation body and bone 8 to get a more stable retention.

Figure 1:
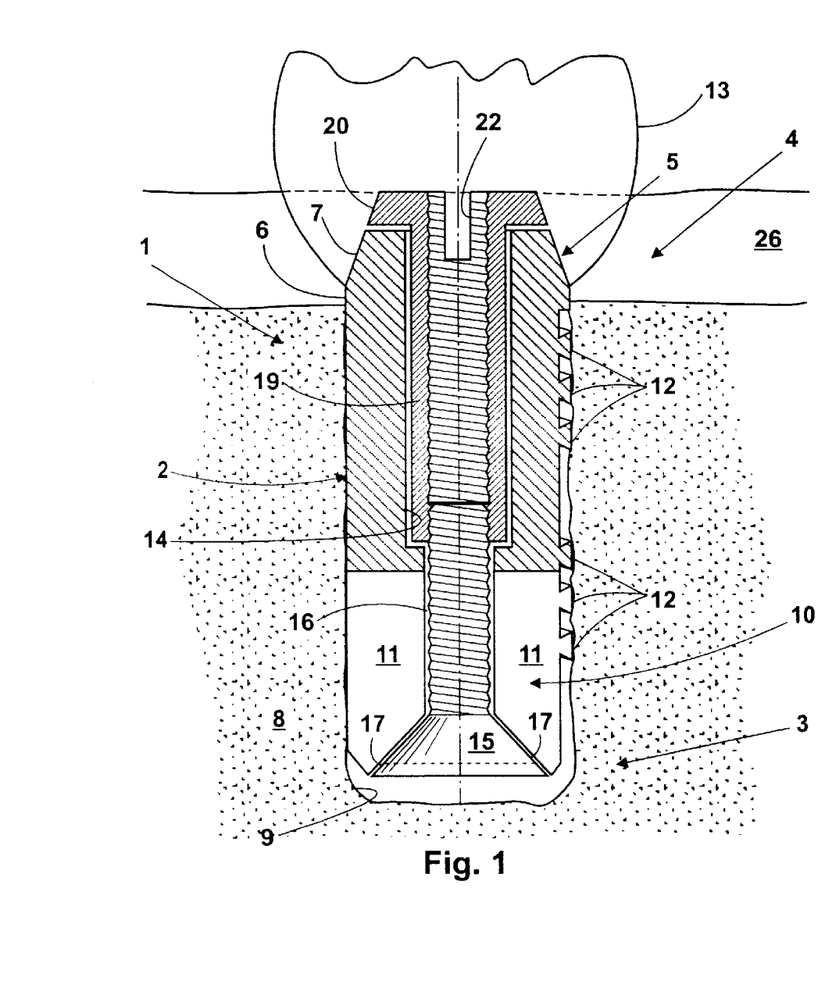
FIG. 1 shows a partially cross-sectional, elevation view of an expandable implant according to a preferred embodiment of the invention.
Figures 2, 3:
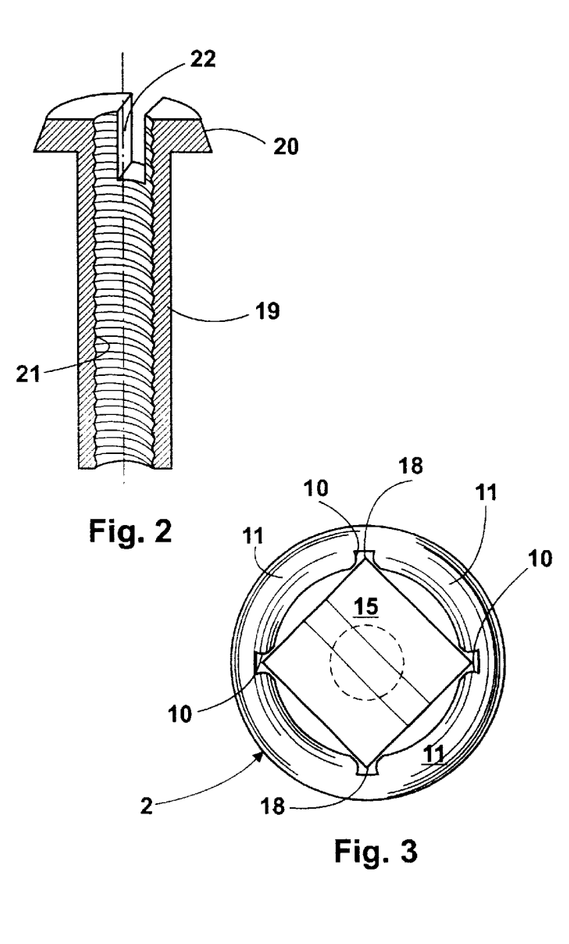
FIG. 2 shows a cross-sectional, perspective view of the mounting intermediate member of FIG. 1.
FIG. 3 shows a plant, bottom view of the implant of FIG. 1.
Figure 4:
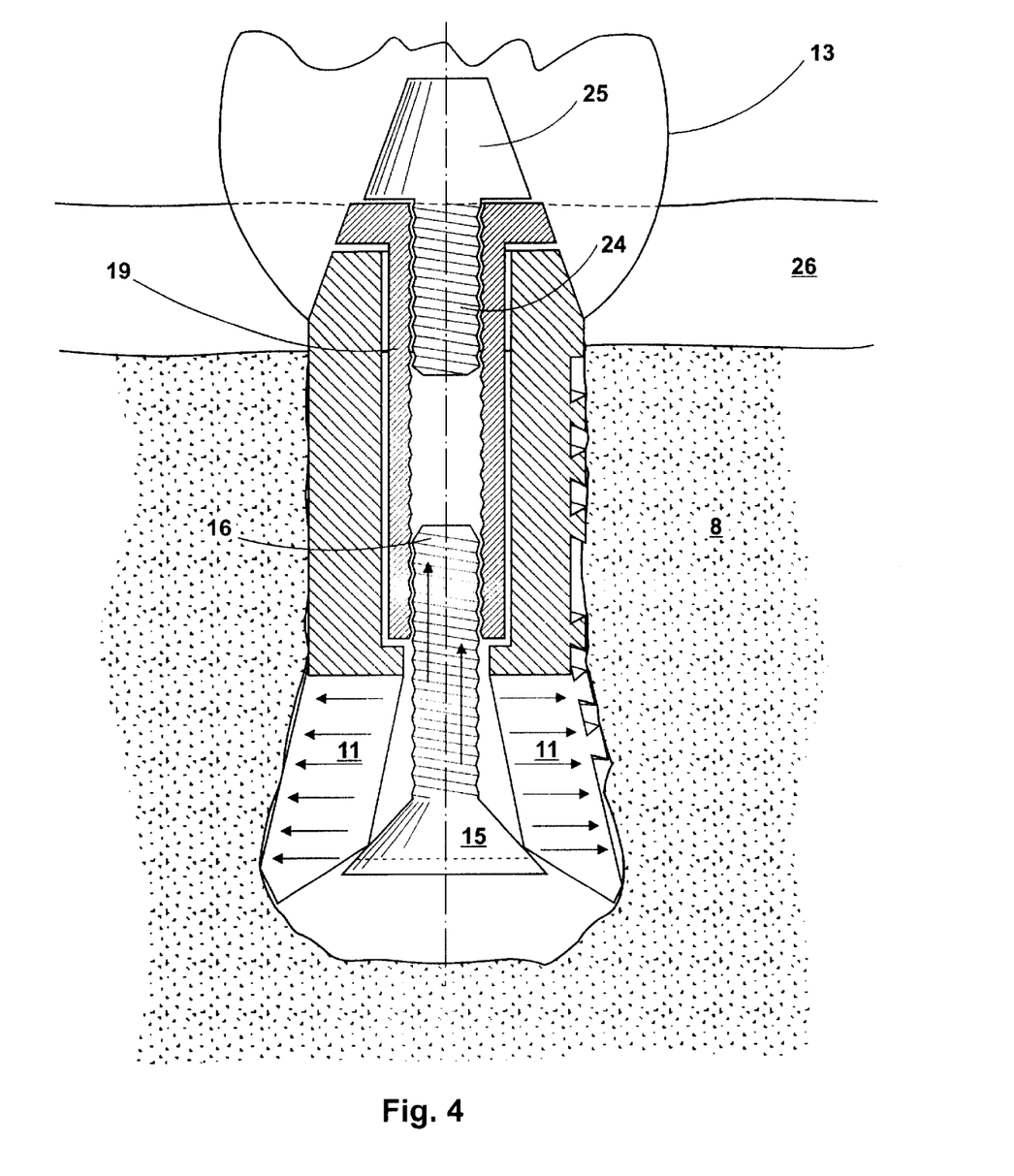
FIG. 4 shows a cross-sectional elevation view of the implant of FIG. 1 once expanded by the expanding member.
Figure 5:
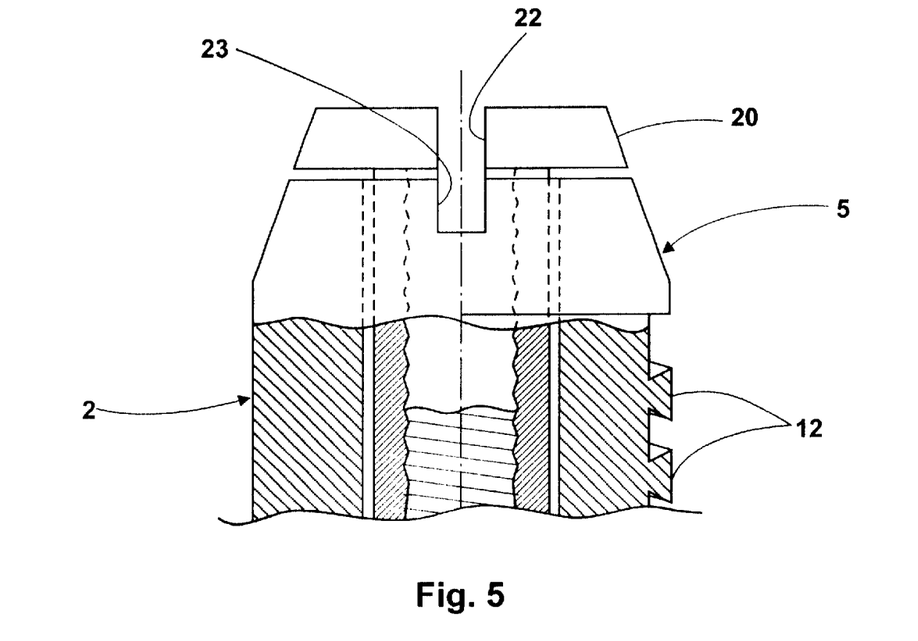
FIG. 5 shows a partial cross-sectional view of a proximal end of the implant of FIG. 1.
Figure 6:
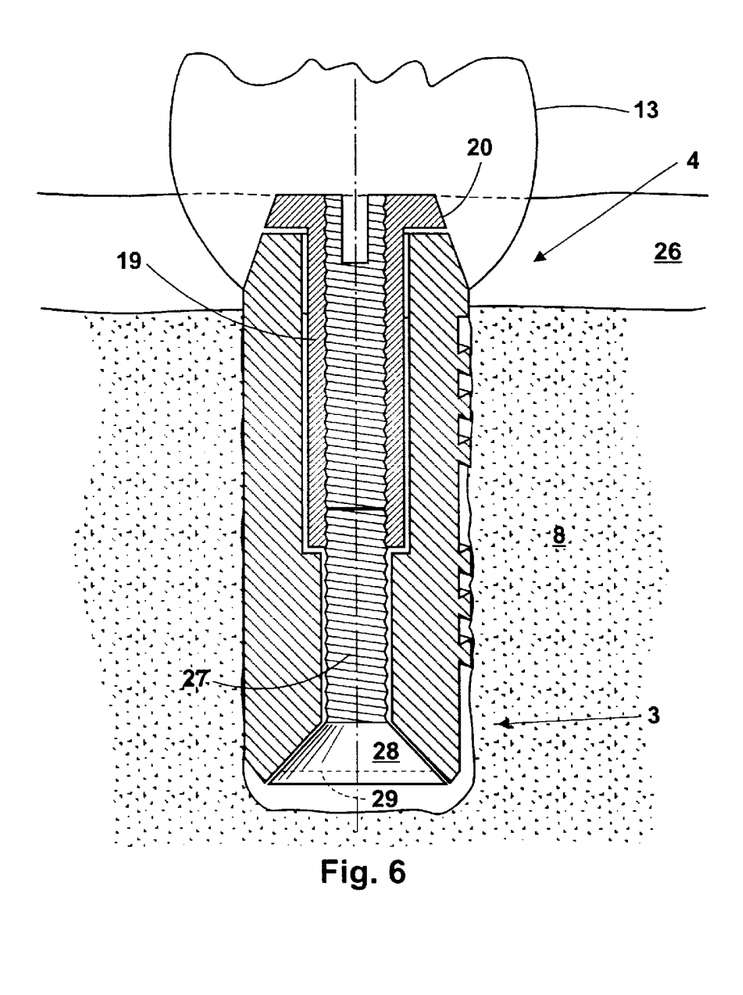
FIG. 6 shows a partially cross-sectional, elevation view of a non expandable implant according to another preferred embodiment of the invention.

Proximal end 4 and more particularly mounting plate 5 remain outside bone 8 and are adapted to receive a dental prosthetic piece 13, schematically illustrated in FIGS. 1, 4 and 6.

Body 2 is hollow and tubular and defines a bore 14 extending along the body and receiving an expanding member 15 having a stem 16 that is threaded along at least a part of the length thereof. While bore 14 is illustrated as being a stepped bore, the bore may be smooth, plain or straight cylindrical from one end to the opposite end. Expanding member 15 has a truncated pyramid configuration with sloped walls 17 of member 15 resting against tongues 11 of body 2 and corners 18 of the truncated pyramid are accommodated within longitudinal cuts 10, whereby any rotation of expanding member 15 is prevented by the locking or wedging effect between member 15 and cuts 10 and tongues 11.

A mounting intermediate member 19 is inserted through proximal end 4, member 19 including, at its proximal end, a coupling plate 20 capable of entering in a mating relationship with the plate or coupling end 5. Plate 20 rests and abuts against end 5. Member 19 has an outer surface, preferably a smooth outer surface, adapted to be accommodated within body 2 and has a threaded interior 21 that receives threaded stem 16 of expanding member or head 15. With this assembly, by rotating intermediate member 19, either in clockwise or counterclockwise direction, a corresponding upward or downward sliding movement of member 15 and stem will be obtained because stem 16 is threadably connected to member 19 along threads 21 and member 15 is prevented from rotating within tongues 11. Upper plate 20 of member 19 is provided with a notch 22 radially extending across the plate and passing through the plate, adapted to receive the tip of a screwdriver for rotating the intermediate member. In like manner, coupling plate 5 is provided with a groove 23 extending radially across end 4 of body 2 and within end 4 along a small depth that is to be covered by prosthesis 13. By rotating intermediate member 19 notch 22 and groove 23 are capable of being placed in mating relationship in order that the tip of a screwdriver may be inserted simultaneously into both the notch and the groove.

During the operation of installing or mounting the implant within bore 9 of bone 8 the implant is arranged with its components assembled as it is shown in FIG. 1, that is member 15 is within distal end 3 with tongues 11 in a non expanded condition. Once the implant is introduced into bore 9 as shown in FIG. 1 a tool, such as a screwdriver, is introduced into notch 22 and it is rotated until notch 22 is aligned with groove 23, see FIG. 5. With notch 22 and groove 23 in this aligned position, the tip of the screwdriver will be not only within notch 22 but also within groove 23, therefore the screwdriver may be rotated in order to rotate all the implant assembly to facilitate the introduction thereof into bore 9. If threads 12 are provided according to an embodiment of the invention, threads 12 will penetrate the bone walls like in a screw and an initial retention of the implant within the bone will be obtained. If threads 12 are not provided the rotation of implant 1 will facilitate in any case the insertion thereof into the bore.

Once the implant has been installed as shown in FIG. 1, the screwdriver is moved slightly upwardly enough to remove the screwdriver tip from groove 23 but retaining the tip into notch 22. Then, the screwdriver is rotated to cause the rotation of intermediate member 19 in such a way to cause the upward movement of stem 16 along thread 21. This upward movement will cause walls 17 of expanding member 15 to exert a radial expanding pressure against tongues 11 and to cause tongues 11 to radially expand against the wall of bore 9 as indicated by the arrows in FIG. 4. Intermediate member would be rotated until a desired retention is achieved between the outer surface of body 2, either with or without threads 12, and the bone.

Prosthesis piece 13 is attached or affixed into intermediate member 19 by means of a fixing pin or stud 24 of an abutment 25, which pin or stud may be smooth or threaded, or partially smooth and partially threaded. The stud/abutment assembly may be only one integral piece or may comprise two or more parts, with a configuration either straight cylindrical or conical, as well as perpendicular or inclined. Depending on whether stud 24 is threaded, as shown in FIG. 4, or smooth (not illustrated), the stud will be threadably retained in corresponding threads 21 of member 19 or retained by adhesive or cement into at least a smooth portion of an inner surface of member 19. All this assembly is covered by prosthesis 13 that extends into gum 26 indicated by a phantom line passing through the prosthesis in FIGS. 1 and 4.

In the event prosthesis 13 is loosened, for example because the stud is broken, which is a frequent accident resulting from the high forces involved in chewing, a new prosthesis must be prepared and installed in the implant. It is to be remarked that when this accident occurs fixing body 2 is already osseous-integrated, that is integrated with the surrounding bone because of the bone growth around and into the parts of the implant. As stated above, the removal of the portion of stud that remains broken in the implant is almost impossible to be carried out and the removal of the entire implant is frequently necessary. According to the invention, if stud is broken within intermediate member 19 and a portion of the stud remains within member 19, the removal of the stud is possible thank to the possibility of removing member 19 by removing the same from body 2. The removal of member 19 is carried out by unscrewing the same either from stem 16, FIGS. 1, 4, 6, or from threads 31 shown in FIG. 8, by using a simple screwdriver or any other proper tool that is inserted into notch 22 only. This removal is possible even with body 2 and member 15/stem 16 are already integrated to the bone, that is completely surrounded and retained by the bone. By unscrewing, member 19 is upwardly removed in order to allow the implantologist to repair the prosthesis by easily removing the broken portion of the stud from member 19 or to install a new intermediate member containing a new prosthesis and stud. This is a remarkable improvement as compared to the prior art because the traumatic removal of the fixing body already integrated to the bone is avoided for the benefit of the patient's comfort and the implantologist's practice.

Figure 7:
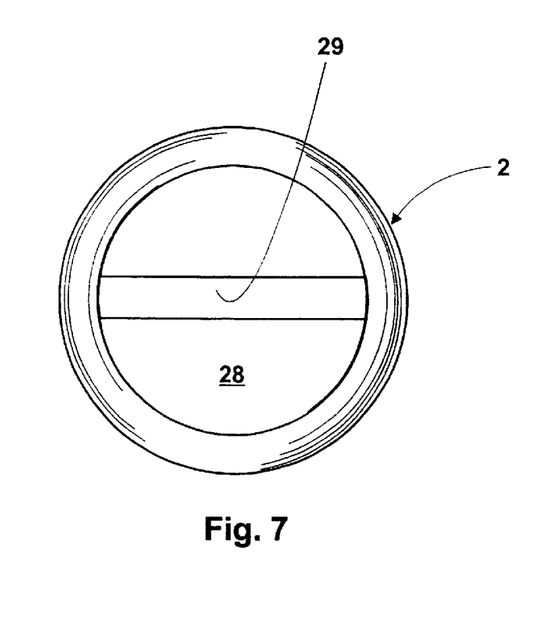
FIG. 7 shows a plant, bottom view of the implant of FIG. 6.

While the concepts of the invention have been illustrated and disclosed in relation to an implant of the expandable type, as illustrated in FIGS. 1–5, it must be understood that the invention is likewise applicable to non-expandable implants such as the one illustrated in FIGS. 6 and 7.

As shown in FIGS. 6, 7, the equivalent components of the invention are identified in these Figures with the same reference numbers of FIGS. 1–5. Thus, intermediate member 19 may be like any of the ones illustrated in FIGS. 1–5, but fixation body 2 of FIGS. 6, 7, differing from body 2 of FIGS. 1–5, has a distal end 3 without cuts 10, that is the body is entirely cylindrical therefore, without expansion capability. Instead of an expanding member 15, a simple screw 27 is provided, the screw having a conventional head 28 provided with an actuating groove 29 for receiving the tip of a screwdriver to rotate the screw and screw the same into intermediate member 19 upon assembling the implant before installing the same into bore 9. The purpose of screw 27 is to retain intermediate member 19 within fixation body 2. After the osseous-integration of body 2 has been completed, if the prosthesis stud (not illustrated in FIG. 6) is broken, intermediate member 19 may be easily removed by unscrewing the same by means of a screwdriver, for example.

Figure 8:
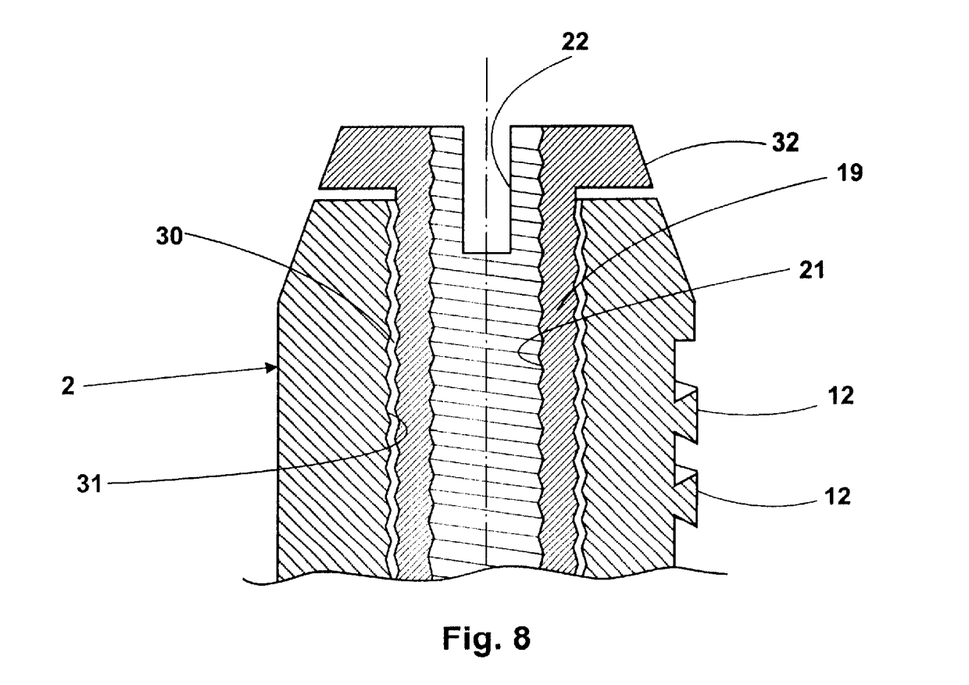
FIG. 8 shows a partial cross-sectional view of a proximal end of the implant according to another embodiment of the invention.

According to another alternative embodiment of the invention, the outer surface of intermediate member 19 has threads 30, along a total or partial length of the member, and bore 14 inside body 2 is provided with threads 31 extending along the entire or partial length of the bore, whereby intermediate member 19 may be threadably and removably mounted within body 2 without the need of any additional screw 27 of FIG. 8. Inner threads 21 and threads 30, 31 and 12 preferably have the same helical sense to prevent member 19 from loosening from body 2, or body from loosening from bore 9, when stud 24 is being screwed into intermediate member 19. Member 19 may define, at its proximal end, a head or plate 32 provided with a groove for receiving a screwdriver, or the head or plate may have a polygonal configuration, quadrangular, hexagonal, for connecting a wrench, for example.

Figure 9:
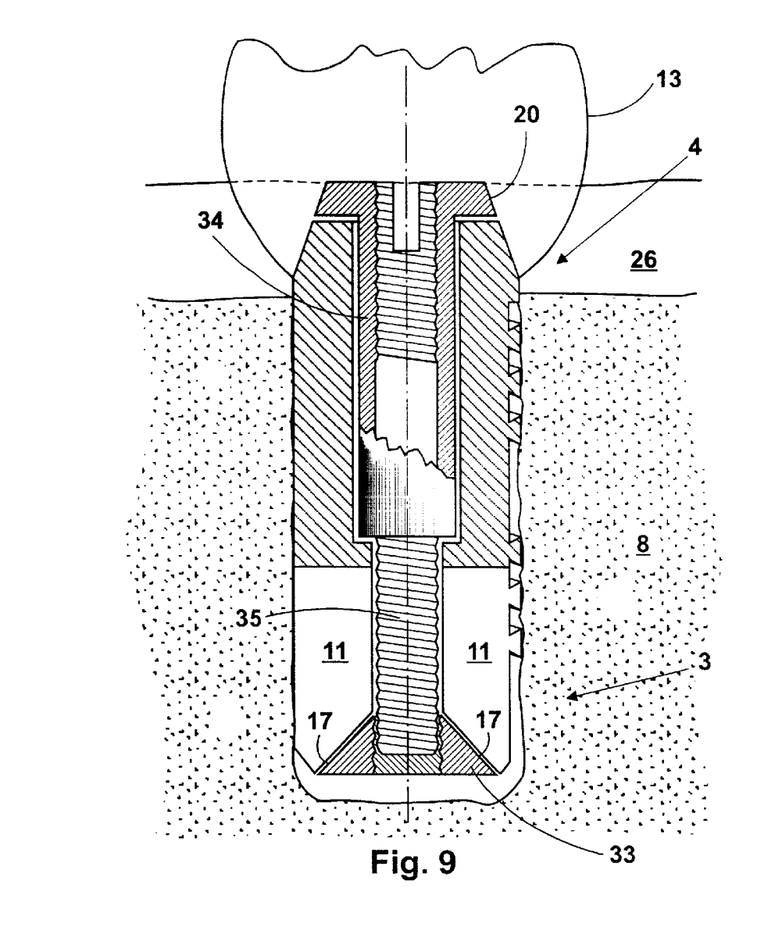
FIG. 9 shows a partially cross-sectional, elevation view of an expandable implant according to another preferred embodiment of the invention.

FIG. 9 shows an expandable bone implant according to another alternative embodiment of the invention wherein the expanding member 15 of FIG. 1 consists of an expanding nut 33 also having sloped walls 17, and threaded stem 16 of FIG. 1 is replaced by stem 35 not joined to the expanding member but to the intermediate member now indicated with reference number 34. Similarly to the assembly of FIG. 1, by rotating intermediate member 34, either in clockwise or counterclockwise direction, a corresponding upward or downward sliding movement of member 33 along stem 35 will be obtained because stem 35 is threadably connected to nut 33 which is prevented from rotating within tongues 11. Stem 35 may be an integral part of intermediate member 34 or may be joined by any proper manner like welding, etc.

Figure 10:
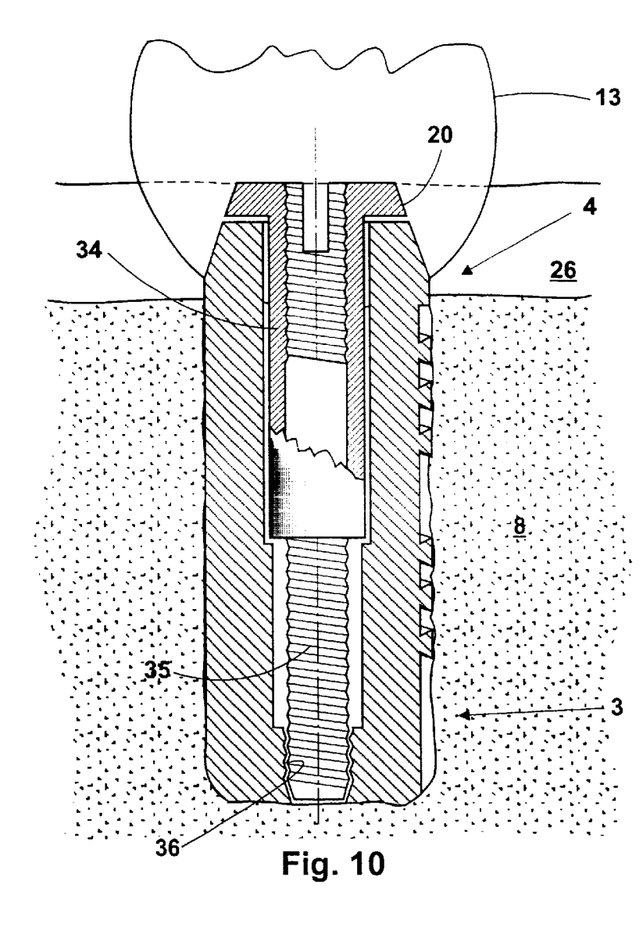
FIG. 10 shows a partially cross-sectional, elevation view of a non expandable implant according to another preferred embodiment of the invention.

According to another alternative embodiment FIG. 10 shows a non expandable implant similar to implant of FIG. 6, wherein a threaded stem 35/intermediate member 34 like the assembly shown in FIG. 9 has been used to replace screw 27/head 28. Since this is a non expandable implant no expanding member is provided and, instead, body 2 is provided with a threaded bottom bore 36 at bottom end 3. Like the above embodiments, member 34 has an inner surface that may be entirely or partially threaded as shown in FIGS. 9, 10, and stud 24 may be, accordingly, a threaded or a smooth stud or a partial threaded and a partial smooth stud.

As it is well clear for any expert in the art, if the abutment or stud of a prosthesis is broken with a portion of the broken stud remaining within intermediate member 19, 34, the stud portion, together with the intermediate member, may be easily removed from the fixation body for repairing the prosthesis and installing a new one.

While preferred embodiments of the present invention have been illustrated and described, it will be obvious to those skilled in the art that various changes and modifications may be made therein without departing from the scope of the invention as defined in the appended claims.

I claim:

1. A bone implant comprising a fixing tubular body for fixing in the bone, the tubular body including a distal end for being affixed within a bone bore and a proximal end for remaining accessible outside the bone and a prosthesis piece being received in the proximal end, the bone implant comprising:

a mounting intermediate member for mounting said prosthesis piece, the intermediate member being rotatably removably mounted within said tubular body;

the intermediate member including a proximal end having a coupling plate abutting directly said proximal end of the tubular body and an inner surface for receiving a fixing stud of said prosthesis piece; and the coupling plate of the intermediate member including means for connecting a tool for easily removing the intermediate member from the tubular body.

2. The bone implant of claim 1, wherein said intermediate member is at least partially threadably fixed into the tubular body.

3. The bone implant of claim 2, wherein said intermediate member defines at its proximal end a plate or head having a polygonal configuration.

4. The bone implant of claim 1, wherein said intermediate member is rotatably attached within the tubular body, said inner surface of the intermediate member being threaded and receives a fixing stem having a proximal end threaded in said threaded inner surface and a distal end having a retention head arranged in said distal end of the tubular body.

5. The bone implant of claim 4, wherein the implant is an expandable implant and the distal end of the tubular body includes a plurality of longitudinal cuts defining an expandable portion that is capable of being radially outwardly expanded by said retention head longitudinally moving along the tubular body, said retention head defining an expanding member fixed at the distal end of the fixing stem and retained against rotation in said distal end of the tubular body but permitted to slide within said tubular body.

6. The bone implant of claim 5, wherein the expanding member has a truncate pyramid shape with its vertexes in said longitudinal cuts of the tubular body.

7. The bone implant of claim 5, wherein the inner surface of the intermediate member is smooth and receives said fixing stud of the prosthesis piece, the stud being smooth and is fixed within the intermediate member by adhesive cement.

8. The bone implant of claim 5, wherein the fixing tubular body has an outer smooth surface treated to enhance its adherence characteristics.

9. The bone implant of claim 1, wherein said inner surface of the intermediate member is at least partially threaded and threadably receives said fixing stud that is at least partially threaded.

10. The bone implant of claim 1, wherein said proximal end of the fixing tubular body and said proximal end of the intermediate member have corresponding coupling plates with one plate abutted against the other.

11. The bone implant of claim 10, wherein the plate of the intermediate mounting member includes a radially extended notch for receiving a screwdriver for rotating the intermediate member, said notch passing through the plate of the intermediate member.

12. The bone implant of claim 11, wherein the plate at the proximal end of the tubular body includes a radial groove for receiving said screwdriver, said groove and said notch being capable of being positioned in a mating relationship.

13. The bone implant of claim 1, wherein the tubular body has an outer surface provided with threads.

14. The bone implant of claim 1, wherein the inner surface of the intermediate member and the stud are partially threaded and partially smooth.

15. The bone implant of claim 1, wherein the outer surface of the intermediate member and the bore of the tubular body have a threaded portion and a smooth portion engaged together.

16. The bone implant of claim 1, wherein said intermediate member is rotatably attached within the tubular body, the intermediate member including a threaded stem that is threaded into a threaded bore of said distal end of the tubular body.

17. The bone implant of claim 1, wherein the implant is an expandable implant, the intermediate member including a threaded stem close to the distal end of the tubular body and the distal end of the tubular body includes a plurality of longitudinal cuts defining an expandable portion that is capable of being radially outwardly expanded by an expanding nut that is threadably mounted on the stem and longitudinally moves along the stem under rotation of the intermediate member, said nut being retained against rotation in said distal end of the tubular body but permitted to slide along said stem of the intermediate member.

18. The bone implant of claim 17, wherein the expanding nut has a truncate pyramid shape with its vertexes in said longitudinal cuts of the tubular body.

19. A bone implant comprising a fixing tubular body for fixing in the bone, the tubular body including a distal end for being affixed within a bone bore and a proximal end for remaining accessible outside the bone and a prosthesis piece being received in the proximal end, the bone implant comprising:

a mounting intermediate member for mounting said prosthesis piece, the intermediate member being removably mounted within said tubular body, the intermediate member including a proximal end in communication with an inner surface for receiving a fixing stud of said prosthesis piece;

said proximal end of the fixing tubular body and said proximal end of the intermediate member have corresponding coupling plates with one plate abutted against the other; and wherein the plate of the intermediate mounting member includes a radially extended notch for receiving a screwdriver for rotating the intermediate member, said notch passing through the plate of the intermediate member.

20. A bone implant comprising a fixing tubular body for fixing in the bone, the tubular body including a distal end for being affixed within a bone bore and a proximal end for remaining accessible outside the bone and a prosthesis piece being received in the proximal end, the bone implant comprising:

a mounting intermediate member for mounting said prosthesis piece, the intermediate member being removably mounted within said tubular body, the intermediate member including a proximal end in communication with an inner surface for receiving a fixing stud of said prosthesis piece; and wherein said intermediate member is rotatably attached within the tubular body, said inner surface of the intermediate member being threaded and receives a fixing stem having a proximal end threaded in said threaded inner surface and a distal end having a retention head arranged in said distal end of the tubular body.

* * * * *